(12) United States Patent
Tamai et al.

(10) Patent No.: US 9,623,078 B2
(45) Date of Patent: Apr. 18, 2017

(54) METHOD FOR TREATING CARDIAC INFARCTION USING HMGB1 FRAGMENT

(71) Applicants: GENOMIX CO., LTD, Osaka (JP); OSAKA UNIVERSITY, Osaka (JP)

(72) Inventors: Katsuto Tamai, Osaka (JP); Sokichi Kamata, Osaka (JP); Yasufumi Kaneda, Osaka (JP); Shigeru Miyagawa, Osaka (JP); Yoshiki Sawa, Osaka (JP); Takehiko Yamazaki, Osaka (JP)

(73) Assignees: GENOMIX CO., LTD., Osaka (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 14/436,906

(22) PCT Filed: Oct. 24, 2013

(86) PCT No.: PCT/JP2013/078758
§ 371 (c)(1),
(2) Date: Apr. 20, 2015

(87) PCT Pub. No.: WO2014/065347
PCT Pub. Date: May 1, 2014

(65) Prior Publication Data
US 2015/0273017 A1    Oct. 1, 2015

(30) Foreign Application Priority Data
Oct. 25, 2012  (JP) .................... 2012-235785

(51) Int. Cl.
*A61K 38/17* (2006.01)
*C07K 14/47* (2006.01)

(52) U.S. Cl.
CPC ...... *A61K 38/1709* (2013.01); *C07K 14/4718* (2013.01)

(58) Field of Classification Search
None
See application file for complete search history.

(56) References Cited

U.S. PATENT DOCUMENTS

| | | | |
|---|---|---|---|
| 3,896,810 A | 7/1975 | Akiyama | |
| 5,661,127 A * | 8/1997 | Bhatnagar | C07K 14/495 424/484 |
| 5,851,986 A | 12/1998 | Takada et al. | |
| 5,902,799 A | 5/1999 | Herrmann et al. | |
| 8,673,580 B2 | 3/2014 | Tamai et al. | |
| 2002/0058019 A1 | 5/2002 | Berenson et al. | |
| 2003/0003482 A1 | 1/2003 | Halle et al. | |
| 2003/0060410 A1 | 3/2003 | Tracey et al. | |
| 2004/0031072 A1 | 2/2004 | La Rosa et al. | |
| 2004/0053841 A1 | 3/2004 | Tracey et al. | |
| 2004/0191246 A1 | 9/2004 | Connelly et al. | |
| 2004/0242481 A1 | 12/2004 | Bianchi et al. | |
| 2004/0265971 A1 | 12/2004 | Sato et al. | |
| 2005/0014255 A1 | 1/2005 | Tang et al. | |
| 2005/0260174 A1 | 11/2005 | Fraser et al. | |
| 2006/0035851 A1 | 2/2006 | Bianchi et al. | |
| 2006/0111287 A1 | 5/2006 | Bianchi | |
| 2006/0127373 A1 | 6/2006 | Son et al. | |
| 2006/0281674 A1 | 12/2006 | Tessier et al. | |
| 2007/0154529 A1 | 7/2007 | Bullerdiek | |
| 2009/0053277 A1 | 2/2009 | Nagaya et al. | |
| 2009/0062187 A1 | 3/2009 | Bianchi et al. | |
| 2009/0202500 A1 | 8/2009 | Tamai et al. | |
| 2009/0280488 A1 | 11/2009 | Okazawa | |
| 2011/0091928 A1 | 4/2011 | Tamai et al. | |
| 2011/0097309 A1 | 4/2011 | Tamai et al. | |
| 2011/0104803 A1 | 5/2011 | Tamai et al. | |
| 2012/0251510 A1 | 10/2012 | Tamai et al. | |
| 2015/0274792 A1 | 10/2015 | Tamai et al. | |

FOREIGN PATENT DOCUMENTS

| | | |
|---|---|---|
| AU | 2003-228099 A1 | 1/2004 |
| AU | 2004-203732 A1 | 7/2004 |
| CA | 2325226 A1 | 5/2001 |
| CA | 2512512 A1 | 7/2004 |
| CA | 2636788 A1 | 5/2008 |
| CN | 1516739 A | 7/2004 |
| CN | 1671742 A | 9/2005 |
| CN | 101374538 A | 2/2009 |
| CN | 102076350 A | 5/2011 |
| CN | 102443064 | 5/2012 |
| CN | 102711777 A | 10/2012 |
| EP | 0 791 601 A2 | 8/1997 |
| EP | 1114862 A2 | 7/2001 |
| EP | 1459759 A1 | 9/2004 |
| EP | 2039367 A1 | 3/2009 |

(Continued)

OTHER PUBLICATIONS

Bianchi et al. The DNA binding site of HMG1 protein is composed of two similar segments (HMG boxes), both of which have counterparts in other eukaryotic regulatory proteins. EMBO J. Mar. 1992;11(3):1055-63.*
Zhou et al. Exogenous high-mobility group box 1 protein injection improves cardiac function after myocardial infarction: involvement of Wnt signaling activation. J Biomed Biotechnol. 2012;2012:1-5. Epub May 21, 2012.*
Bustin, Michael, "Regulation of DNA-Dependent Activities by the Functional Motifs of the High-Mobility-Group Chromosomal Proteins", *Molecular and Cellular Biology*, Aug. 1999, pp. 5237-5246, vol. 19, No. 8.
Germani, Antonia et al., "Pivotal Advance: High-Mobility Group Box 1 Protein—A Cytokine with a Role in Cardiac Repair", *Journal of Leukocyte Biology*, Jan. 2007, pp. 41-45, vol. 81.
Hori, Osamu et al., "The Receptor for Advanced Glycation End Products (RAGE) Is a Cellular Binding Site for Amphoterin", *The Journal of Biological Chemistry*, Oct. 27, 1995, pp. 25752-25761, vol. 270, No. 43, Printed in USA.

(Continued)

*Primary Examiner* — David Romeo
(74) *Attorney, Agent, or Firm* — Saliwanchik, Lloyd & Eisenschenk (57) ABSTRACT

A fragment peptide having a proper length composed of a part of an HMGB1 protein was synthesized and the peptide was confirmed to exhibit therapeutic effects on myocardial infarction.

1 Claim, 5 Drawing Sheets

(56) References Cited

FOREIGN PATENT DOCUMENTS

| | | |
|---|---|---|
| EP | 2055308 A1 | 5/2009 |
| EP | 2284255 A1 | 2/2011 |
| EP | 2 301 559 A1 | 3/2011 |
| EP | 2301559 A1 | 3/2011 |
| JP | H09-227403 | 9/1997 |
| JP | 2001-321434 A | 11/2001 |
| JP | 2003-505506 A | 2/2003 |
| JP | 2005-508913 A | 4/2005 |
| JP | 2005-512507 | 5/2005 |
| JP | 2005-537253 | 12/2005 |
| JP | 2006-124389 A | 5/2006 |
| JP | 2006-517537 A | 7/2006 |
| JP | 2006-523085 A | 10/2006 |
| JP | 2007-320919 A | 12/2007 |
| JP | 2008-507505 A | 3/2008 |
| KR | 20090078304 A | 7/2009 |
| RU | 2005102593 A | 10/2005 |
| RU | 2 410 125 C2 | 1/2011 |
| WO | WO 01/08683 A1 | 2/2001 |
| WO | WO 02/074337 A1 | 9/2002 |
| WO | WO 02/088181 A2 | 11/2002 |
| WO | WO 02/092004 A2 | 11/2002 |
| WO | WO 03/026691 A2 | 4/2003 |
| WO | WO 03/043651 A1 | 5/2003 |
| WO | WO 2004/004763 A2 | 1/2004 |
| WO | WO 2004/004770 A1 | 1/2004 |
| WO | WO 2004/044001 A2 | 5/2004 |
| WO | WO 2004/046345 A2 | 6/2004 |
| WO | WO 2004/061456 A2 | 7/2004 |
| WO | WO 2005/025604 A2 | 3/2005 |
| WO | WO 2005/074984 A1 | 8/2005 |
| WO | WO 2006/008779 A1 | 1/2006 |
| WO | WO 2006/010628 A1 | 2/2006 |
| WO | WO 2006/024547 A2 | 3/2006 |
| WO | WO 2006/047820 A1 | 5/2006 |
| WO | WO 2006/077614 A1 | 7/2006 |
| WO | WO 2006/080434 A1 | 8/2006 |
| WO | WO 2006/100651 A1 | 9/2006 |
| WO | WO 2006/114805 A2 | 11/2006 |
| WO | WO 2007/015546 A1 | 2/2007 |
| WO | WO 2007/031100 A1 | 3/2007 |
| WO | WO 2007-130725 A | 11/2007 |
| WO | WO 2008/018641 A1 | 2/2008 |
| WO | WO 2008/053892 A1 | 5/2008 |
| WO | WO 2009/133939 A1 | 11/2009 |
| WO | WO 2009/133940 A1 | 11/2009 |
| WO | WO 2009/133943 A1 | 11/2009 |
| WO | WO 2011/046570 A1 | 4/2011 |
| WO | WO 2011/052668 A1 | 5/2011 |
| WO | WO 2012/147470 A1 | 11/2012 |
| WO | WO 2014/065347 A1 | 5/2014 |
| WO | WO 2014/065348 A1 | 5/2014 |

OTHER PUBLICATIONS

Kitahara, Tatsuro et al., "High-Mobility Group Box 1 Restores Cardiac Function After Myocardial Infarcation in Transgenic Mice", *Cardiovascular Research, European Society of Cardiology*, Oct. 1, 2008, pp. 40-46, vol. 80.

Kohno, Takashi et al., "High Mobility Group Box 1 Protein is Associated With Post-Infarction Healing Process and Left Ventricular Remodeling", *Circ. J.*, 2008, pp. 510-511, 72 Supplement 1, PJ-004.

Limana, Federica et al., "Exogenous High-Mobility Group Box 1 Protein Induces Myocardial Regeneration After Infarction via Enhanced Cardiac C-Kit + Cell Proliferation and Differentiation", *Circulation Research, Journal of the American Heart Association*, 2005, pp. 73-83, 97.

Merenmies, Jussi et al., "30-kDa Heparin-binding Protein of Brain (Amphoterin) Involved in Neurite Outgrowth", *The Journal of Biological Chemistry*, Sep. 5, 1991, pp. 16722-16729, vol. 266, No. 25.

Müller, Susanne et al., "The Double Life of HMGB1 Chromatin Protein: Architectural Factor and Extracellular Signal", *The EMBO Journal*, 2001, pp. 4337-4340, vol. 20 No. 16.

Palumbo, Roberta et al., "Extracellular HMGB1, a Signal of Tissue Damage, Induces Mesoangioblast Migration and Proliferation", *The Journal of Cell Biology*, 2004, pp. 441-449, vol. 164, No. 3.

Takahashi, Kunihiko et al., "Effects of HMGB1 on Postinfarction Chronic Heart Failure—Novel Mechanism Regarding Therapeutic Effects of Cell Therapy", *Supplement*, 2011, p. S189, 27 I-E-19.

Takeishi, Yasuchika et al., "Importance of Inflammation and Immune Response in Heart Failure—Toll-Like Receptor-Mediated Signaling Pathway and Ventricular Remodeling After Myocardial Infarction", *Journal of Clinical and Experimental Medicine*, Jan. 30, 2010, pp. 378-385, vol. 232 No. 5.

Tamai, Katsuto et al., "Development and Outlook of Internal Regeneration-Inducing Pharmaceuticals that use in vivo Bone Marrow Mesenchymal Stem / Progenitor Cell-Mobilizing Factors", *Gene & Medicine MOOK*, Jul. 22, 2012, pp. 207-212.

Tamai, Katsuto et al., "PDGFRα-Positive Cells in Bone Marrow are Mobilized by High Mobility Group Box 1 (HMGB1) to Regenerate Injured Epithelia", *Proceedings of the National Academy of Sciences*, Apr. 19, 2011, 6609-6614, vol. 108, No. 16.

Wang, Haichao et al., "HMG-1 as a Late Mediator of Endotoxin Lethality in Mice", *Science*, www.sciencemag.org, Jul. 9, 1999, pp. 248-251, vol. 285.

Wu, Yaojiong et al., "Mesenchymal Stem Cells Enhance Wound Healing Through Differentiation and Angiogenesis", *Stem Cells—Translational and Clinical Research*, Oct. 2007, pp. 2648-2659, vol. 25, No. 10.

Yang, De et al., "High Mobility Group Box-1 Protein Induces the Migration and Activation of Human Dendritic Cells and Acts as an Alarmin", *Journal of Leukocyte Biology*, Jan. 2007, pp. 59-66, vol. 81.

Tamai, Katsuto et al., U.S. Appl. No. 11/997,475, "Mesenchymal Stem Cell Inducer, Tissue Regeneration Promoter and Method of Preparing Mesenchymal Stem Cell", filed Jan. 31, 2008.

Tamai, Katsuto et al., U.S. Appl. No. 14/114,395, "Peptide for Inducing Regeneration of Tissue and Use Thereof", filed Feb. 6, 2014, assigned to Genomix Co. Ltd. and Osaka University.

International Search Report dated Dec. 3, 2013, for International Application No. PCT/JP2013/078758.

Chamberlain, Giselle et al., "Concise Review: Mesenchymal Stem Cells: Their Phenotype, Differentiation Capacity, Immunological Features, and Potential for Homing," *Stem Cells* 2007; 25:2739-2749.

Kessler, Michael W. et al., "Tissue Engineering and Cartilage," *Organogenesis*, Jan. 2008; 4(1):28-32.

Lanza, Robert et al., and Arnold Caplan, "Essentials of Stem Cell Biology—Chapter 27, Mesenchymal Stem Cells," *Elsevier Academic Press*, 2006, pp. 205-210.

De Souza, A.W.S. et al., "HMGB1 in Vascular Diseases: Its Role in Vascular Inflammation and Atherosclerosis," *Autoimmunity Reviews*, 2012, 11:909-917.

Zhou, Xiaoya et al., "Exogenous High-Mobility Group Box 1 Protein Injection Improves Cardiac Function after Myocardial Infarction: Involvement of Wnt Signaling Activation," *Journal of Biomedicine and Biotechnology*, 2012, vol. 2012, pp. 1-5.

Wang, Huan Liang et al., "High Mobility Group Protein B1 and the Research Progress of its Biological Effect," *Journal of Chinese Modern Surgery*, Dec. 31, 2006, 3(22):1806-1809.

Wang, Huating et al., "Theories and Technologies for Stem Cells," *Series of the 21st Century Biotechnologies*, 2005, pp. 58-61.

Wexler, Sarah A. et al., "Adult Bone Marrow is a Rich Source of Human Mesenchymal 'Stem' Cells but Umbilical Cord and Mobilized Adult Blood Are Not," *British Journal of Haematology*, 2003, 121(2):368-374.

Youn, Ju Ho et al., "High Mobility Group Box 1 Protein Binding to Lipopolysaccharide Facilitates Transfer of Lipopolysaccharide to CD14 and Enhances Lipopolysaccharide-Mediated TNF-α Production in Human Monocytes," *Journal of Immunology*, 2008, 180(7):5067-74.

Yuan, Yan et al., "Differentiation of Mesenchymal Stem Cells in Cardiomyogenic Cells Under the Induction of Myocardial Cell Lysate," *Chinese Journal of Cardiology*, 2005, 33(2):170-173.

(56) References Cited

OTHER PUBLICATIONS

Gudjonsson, Johann E. et al. "Psoriasis," *Fitzpatrick's Dermatology in General Medicine*, 8th edition, New York: Mc-Graw Hill Medical, 2012, pp. 197-217.

Wang, Lei et al., "Ischemic cerebral tissue and MCP-1 enhance rat bone marrow stromal cell migration in interface culture," *Experimental Hematology*, 2002, 30:831-836.

Yamada, Takayuki et al., "Regulation of osteoclast development by Notch signaling directed to osteoclast precursors and through stromal cells," *Blood*, Mar. 2003, 101(6):2227-2234.

Li, Zihai et al., "Heat-Shock Proteins," *Current Protocols in Immunology*, 2003, Supplement 58, A.IT.1-A.IT.6.

Martin-Murphy, Brittany V. et al., "The Role of Damage Associated Molecular Pattern Molecules in Acetaminophen-Induced Liver Injury in Mice," *Toxicol Lett*, Feb. 2010, 192(3):1-20.

Panepucci, Rodrigo A. et al., "Abstract# 4427: Comparison of Gene Expression of Mesenchymal Stem Cells from the Umbilical Cord and from the Bone Marrow," *Blood*, Nov. 2003, 16(102):Abstract.

Pankov, Roumen et al., "Fibronectin at a glance," *J Cell Sci*, Oct. 2002, 115(20):3861-3863.

Santamaria-Kiseil, Liliana et al., "Calcium-dependent and -independent interactions of the S100 protein family," *Biochem J.*, 2006, 396:201-214.

Seong, Yong Seong et al., "Hydrophobicity: an ancient damage-associated molecular pattern that initiates innate immune responses," *Nature Reviews: Immunology*, Jun. 2004, 4(6):469-78.

Soo, Eliza T. L. et al., "Heat Shock Proteins as Novel Therapeutic Targets in Cancer," in vivo, 2008, 22(3):311-5.

"Isolating Culture and Induced Differentiation of Marrow Mesenchyma Stem Cells," *Principles and Protocols of Tissue Engineering*, Jun. 2004, pp. 277-278. See English Translation.

Alden, Tord at al., "In Vivo Endochondral Bone Formation Using a Bone Morphogenetic Protein 2 Adenoviral Vector," *Human Gene Therapy*, Sep. 1, 1999, 10(13):2245-2253.

Basso, D. Michelle et al., "Basso Mouse Scale for Locomotion Detects Differences in Recovery after Spinal Cord Injury in Five Common Mouse Strains," *Journal of Neurotrauma*, 2006, 23(5):635-659.

Bittira, Bindu et al., "Mobilization and Homing of Bone Marrow Stromal Cells in Myocardial Infarction," *European Journal of Cardio-thoracic Surgery*, Sep. 2003, 24(3):393-398.

Castro, Raymond F. at al., "Failure of Bone Marrow Cells to Transdifferentiate into Neural Cells in Vivo," *Science*, 2002, 297(5585):1299.

Charoonpatrapong, Kanokwan et al., "HMGB1 Expression and Release by Bone Cells," *Journal of Cellular Physiology*, 2006, 207(2):480-490.

Chen, Xiaoguang et al., "Human Bone Marrow Stromal Cell Cultures Conditioned by Traumatic Brain Tissue Extracts: Growth Factor Production," *Journal of Neuroscience Research*, 2002, 69:687-691.

Chen, Y. et al., "Coaxing Bone Marrow Stromal Mesenchymal Stem Cells Towards Neuronal Differentiation: Progress and Uncertainties," *Cellular and Molecular Life Sciences*, 2006, 63(14):1649-1657.

Chopp, Michael et al., "Treatment of Neural Injury with Narrow Stromal Cells," *The Lancet Neurology*, 2002, 1(2):92-100.

Chou, Denise et al., "Identity of Nuclear High-Mobility-Group Protein, HMG-1, and Sulfoglucuronyl Carbohydrate-Binding Protein, SBP-1, in Brain," *Journal of Neurochemistry*, 2001, 77:120-131.

Degryse, Bernard et al., "The High Mobility Group (HMG) Boxes of the Nuclear Protein HMG1 Induce Chemotoxins and Cytoskeleton reorganization in Rat Smooth Muscle Cells," *The Journal of Cell Biology*, 2001, 152(6):1197-1206.

Delarosa, Olga et al., "Modulation of Adult Mesenchymal Stem Cells Activity by Toll-Like Receptors: Implications on Therapeutic Potential," *Mediators of inflammation*, Jun. 14, 2010, 2010: 1-9.

Eckert, Richard et al., "S100 Proteins in the Epidermis," *The Journal of Investigative Dermatology*, Jul. 2004, 123(1):23-33.

Ehrchen, Jan M. et al., "The Endogenous Toll-like Receptor 4 Agonist S100A8/S100A9 (calprotectin) as Innate Amplifier of Infection, Autoimmunity, and Cancer," *Journal of Leukocyte Biology*, 2009, 86: 557-566.

Erlandsson, Helena et al. "The Nuclear Protein HMGB1 as a Proinflammatory Mediator," *European Journal of Immunology*, 2004, 34(6):1503-1512.

Fang, Ping et al., "HMGB1 Contributes to Regeneration After Spinal Cord Injury in Adult Zebrafish," *Mol Neurobiol*, 2014, 49:472-483.

Forte, Giancarlo et al., "Hepatocyte Growth Factor Effects on Mesenchymal Stem Cells: Proliferation, Migration, and Differentiation," *Stem Cells*, 2006, 24(1):23-33.

Fujii, Makiko et al., "Roles of Bone Morphogenetic Protein Type I Receptors and Smad Proteins in Osteoblast and Chondroblast Differentiation," *Molecular Biology of the Cell*, Nov. 1999, 10(11):3801-3813.

Granero-Molto, Froilan et al., "Role of Mesenchymal Stem Cells in Regenerative Medicine: Application to Bone and Cartilage Repair," *Expert Opinion on Biological Therapy*, Mar. 2008, 8(3):255-268.

Gueukdjian, S.A., "Intra-Arterial Injections in the Treatment of Peripheral Vascular Disease," *Postgrad Medical Journal*, Jan. 1955, 31(351):30-31.

Harris, Helena et al., "Alarmin(g) News About Danger," *EMBO Reports*, 2006, 7(8):774-778.

Heil, Matthias et al., "An Engineered Heparin-Binding Form of VEGF-E (hbVEGF-E): Biological Effects in Vitro and Mobilization of Precursor Cells," *Angiogenesis*, 2003, 6(3):201-211.

Hiratsuka, Sachie et al., "Tumor-mediated Upregulation of Chemoattractants and Recruitment of Myeloid Cells Predetermines Lung Metastasis," *Nature Cell Biology*, Dec. 2006, 8(12):1369-1375.

Huttunen, Henri J. et al., "Receptor for Advanced Glycation End Products-binding COOH-terminal Motif of Amphoterin Inhibits Invasive Migration and Metastasis," *Cancer Research*, 2002, 62(16):4805-4811.

Institutional Animal Care and Use Committee (IACUC), "Blood Collection: The Mouse," University of California, San Francisco, May 2014, Taken from web: iacuc.usfc.edu/Policies/BloodCollectionMice.doc.

Instruction Manual of HiTrap Chelating HP, *Amersham Biosciences*, 2003, pp. 1-6.

Jansen, Jan et al., "Transplantation of Hematopoietic Stem Cells from the Peripheral Blood," *Journal of Cellular and Molecular Medicine*, (Jan.-Mar.) 2005, 9(1):37-50.

Jayaraman, Lata et al., "High Mobility Group Protein-1 (HMG-1) is a Unique Activator of ?p. 53," *Genes & Development*, 1998, 12:462-472.

Jiang, Yuehua et al., "Pluripotency of Mesenchymal Stem Cells Derived from Adult Marrow," *Nature*, Jul. 4, 2002, 418(6893):41-49.

Kassis, I. et al., "Isolation of Mesenchymal Stem Cells from G-CSF-Mobilized Human Peripheral Blood using Fibrin Microbeads," *Bone Marrow Transplantation*, May 2006, 37(10):967-76.

Kern, Susanne et al., "Comparative Analysis of Mesenchymal Stem Cells from Bone Marrow, Umbilical Cord Blood, or Adipose Tissue," *Stem Cells*, 2006, 24(5):1294-1301.

Kim, Sang-Soo et al., "Skin Regeneration Using Keratinocytes and Dermal Fibroblasts Cultured on Biodegradable Microspherical Polymer Scaffolds," *Journal of Biomedical Materials Research Part: Applied Biomaterials*, Nov. 2005, 75(2): 369-377.

Koc, On et al., "Mesenchymal Stem Cells: Heading into the Clinic," *Bone Marrow Transplantation*, 2001, 27(3):235-239.

La Rosa, TJ et al., "Glycine max protein SEQ ID No. 211221," Geneseq Accession No. AFQ20044, 2007.

Laflamme, Michael et al., "Regenerating the Heart," *Nature Biotechnology*, Jul. 2005, 23(7):845-856.

Li, Huang et al., "Millennium Review: Nonviral Gene Therapy: Promises and Challenges," *Gene Therapy*, 2000, 7(1):31-34.

Lin, Siang-Yo et al., "The Isolation of Novel Mesenchymal Stromal Cell Chemotactic Factors from the Conditioned Medium of Tumor Cells," *Experimental Cell Research*, 2008, 314(17):3107-3117.

(56) References Cited

OTHER PUBLICATIONS

Liotta, Francesco et al., "Toll-Like Receptors 3 and 4 Are Expressed by Human Bone Marrow-Derived Mesenchymal Stem Cells and Can Inhibit Their T-Cell Modulatory Activity by Impairing Notch Signaling," *Stem Cells*, Jan. 2008, 26(1):279-289.
Liu, Ke-Xin et al., "Human Placental Extract Stimulates Liver Regeneration in Rats," *Biological and Pharmaceutical Bulletin*, 1998, 21(1):44-49.
Lonza BenchGuides, "Poietics Human Mesenchymal Stem Cells and Media hMSC," 2008, (Document # TS-PT-212-7 Apr. 2008).
Mansbridge, Jonathan, "Skin Tissue Engineering," *J. Biomater. Sci. Polymer Ed.*, Aug. 1, 2008, 19(8):955-968.
Maruyama, Ikuro, "Inflammation and HMGB1/Rage system," *Kekkan Igaku*, 2005, 6(5):519-525. See English translation.
Matsumoto, Kunio et al., "Up-Regulation of Hepatocyte Growth Factor Gene Expression by Interleukin-1 in Human Skin Fibrosis," *Biochemical and Biophysical Research Communications*, 1992, 188(1):235-243.
Meng, Er-Hong et al., "HMGB1 Induces Migration of Human Bone Marrow-Derived Mesenchymal Stem Cells," *Bull Acad Mil Med Sci*, Jun. 2006, 30(3):213-216.
Meng, Erhong et al., "High Mobility Group Box 1 Protein Inhibits the Proliferation of Human Mesenchymal Stem Cells and Promotes Their Migration and Differentiation along Osteoblastic Pathway," *Stem Cells and Development*, 2008, 17:805-814.
Mistry, A.R. et al., "Recombinant HMG1 Protein Produced in *Pichia pastoris*: A Nonviral Gene Delivery Agent," *BioTechniques*, Apr. 1997, 22:718-729.
Mori, Taisuke et al., "Stem Cells / ES cells—Mesenchymal Stem Cells—Human Bone Marrow Derived Mesenchymal Stem Cells," *Saisei Iryou—Regenerative Medicine*, 2005, 4(3); 421-9, 351.
Muhammad, Sajjad et al. "The HMGB1 Receptor RAGE Mediates ischemic Brain Damage," *The Journal of Neuroscience*, Nov. 12, 2008, 28(46):12023-12031.
Nakajima et al., "Dynamics and Role of High Mobility Group Box-1 (HMGB-1) in Injured Spinal Cord," *Nihon Seikei Geka Gakkai Zasshi (J. Jpn. Orthop. Assoc.)*, 2010, 84(8):S1050.
Nakamura, Koji et al., "p38 Mitogen-Activated Protein Kinase Functionally Contributes to Chondrogenesis Induced by Growth/Differentiation Factor-5 in ATDC5 Cells," *Experimental Cell Research*, Aug. 1, 1999, 250(2):351-363.
Opitz, Christine A. et al., "Toll-like Receptor Engagement Enhances the Immunosuppressive Properties of Human Bone Marrow-Derived Mesenchymal Stem Cells by Inducing Indoleamine-2,3-dioxygenase-1 via Interferon-β and Protein Kinase R," *Stem Cells*, Apr. 2009, 27(4):909-919.
Otsuru, Satoru et al., "BMP-2 mobilizes robust bone marrow mesenchymal progenitor cells to the circulating blood in bone regeneration," *The 28th Annual Meeting of the Molecular Biology Society of Japan*, Nov. 25, 2005, 733(3P-1012).
Ozaki, Yoshie et al., "Comprehensive Analysis of Chemotactic Factors for Bone Marrow Mesenchymal Stem Cells," *Stem Cells and Development*, Feb. 2007, 16(1):119-29.
Palumbo, Roberta et al., "Cells migrating to sites of tissue damage in response to the danger signal HMGB1 require NF-κB activation," *The Journal of Cell Biology*, Oct. 8, 2007, 179(1):33-40.
Palumbo, Roberta et al., "High Mobility Group Box 1 Protein, a Cue for Stem Cell Recruitment," *Biochemical Pharmacology*, 2004, 68:1165-1170.
Paul, S.R. et al., "Stromal Cell-Associated Hematopoiesis: Immortalization and Characterization of a Primate Bone Marrow-Derived Stromal Cell Line," *Blood*, 1991, 77(8):1723-1733.
Pevsner-Fischer, Meirav et al., "Toll-like receptors and their ligands control mesenchymal stem cell functions," *Blood*, Feb. 15, 2007, 109(4):1422-1432.
Pittenger, Mark F. et al., "Multilineage Potential of Adult Human Mesenchymal Stem Cells," *Science*, Apr. 1999, 284(5411):143-147.
Popovic, Karin et al., "Increased Expression of the Novel Proinflammatory Cytokine High Mobility Group Box Chromosomal Protein 1 in Skin Lesions of Patients With Lupus Erythematosus," *Arthritis & Rheumatism*, 2005, 52(11):3639-3645.
Pusterla, Tobias et al., "High Mobility Group B2 is Secreted by Myeloid Cells and has Mitogenic and Chemoattractant Activities Similar to High Mobility Group B1," *Autoimmunity*, Apr. 2009, 42(4):308-310.
Quertainmont, Renaud et al., "Mesenchymal Stem Cell Graft Improves Recovery after Spinal Cord Injury in Adult Rats through Neurotrophic and Pro-Angiogenic Actions," *PLoS ONE*, Jun. 2012, 7(6):1-15.
Rahimi-Movaghar, Vafa et al., "Effect of Decompression on Complete Spinal Cord Injury in Rats," *International Journal of Neuroscience*, 2008, 118:1359-1373.
Raicevic Gordana, et al., "Inflammation Modifies the Pattern and the Function of Toll-like Receptors Expressed by Human Mesenchymal Stromal Cells," *Human Immunology*, Mar. 2010, 71(3):235-244.
Robinson, Matthew J. et al., "The S100 Family Heterodimer, MRP-8/14, Binds with High Affinity to Heparin and Heparan Sulfate Glycosaminoglycans on Endothelial Cells," *The Journal of Biological Chemistry*, Feb. 2002, 277(5):3658-3665.
Ryckman, Carle et al., "Proinflammatory Activities of S100: Proteins S100A8, S100A9, and S100A8/A9 Induce Neutrophil Chemotaxis and Adhesion," *The Journal of Immunology*, Mar. 15, 2003, 170(6):3233-3242.
Sasaki, Mikako et al., "Mesenchymal Stem Cells Are Recruited into Wounded Skin and Contribute to Wound Repair by Transdifferentiation into Multiple Skin Cell Type[1]," *The Journal of Immunology*, Feb. 15, 2008, 180(4):2581-7.
Schäffer, Michael R. et al., "Wound Fluid Inhibits Wound Fibroblast Nitric Oxide Synthesis," *Journal of Surgical Research*, Nov. 2004, 122(1):43-48.
Schön, Michael P. et al., "Psoriasis," *The New England Journal of Medicine*, May 5, 2005, 352(18):1899-1912.
Shibata Futoshi et al., "Fibroblast Growth-Stimulating Activity of S100A9 (MRP-14)," *European Journal of Biochemistry*, Jun. 2004, 271(11):2137-2143.
Shing, Y et al., "Heparin Affinity: Purification of a Tumor-Derived Capillary Endothelial Cell Growth Factor," *Science*, Mar. 23, 1984, 223(4642):1296-1299.
Somia, Nikunj et al., "Gene Therapy: Trials and Tribulations," *Nat. Rev. Genet.*, 2000, 1(2):91-99.
Sun, Shengkun et al., "Isolation of Mouse Marrow Mesenchymal Progenitors by a Novel and Reliable Method," *Stem Cells*, 2003, 21(5):527-535.
Tagami, Kozo et al., "Elevation of Serum High-Mobility Group Box 1 Protein During Granulocyte Colony-Stimulating Factor-Induced Peripheral Blood Stem Cell Mobilisation," *British Journal of Haematology*, Oct. 10, 2006, 135(4):567-569.
Tagliafico, Enrico et al., "TGFβ/BMP Activate the Smooth Muscle/Bone Differentiation Programs in Mesoangioblasts," *Journal of Cell Science*, 2004, 117(Pt 19):4377-88.
Takami, Yoichiro et al., "Synergistic Induction of Hepatocyte Growth Factor in Human Skin Fibroblasts by the Inflammatory Cytokines Interleukin-1 and Interferon-γ," *Biochemical and Biophysical Research Communications*, 2005, 327(1):212-217.
Tamai, Katsuto et al., "New Wave of Wound Healing," *Japanese Journal of Dermatology*, 2008, 118(4):645, #EL28-4. See English translation.
Tamai, Katsuto et al., "PDGFRα-positive Cells in Bone Marrow are Mobilized by High Mobility Group Box 1 (HMGB1) to Regenerate Injured Epithelia," http://www.pnas.org/content/suppl/2011/03/31/1016753108.DCSupplemental/pnas.201016753SI.pdf, Apr. 4, 2011.
Tatsumi, Ryuichi et al., "HGF/SF Is Present in Normal Adult Skeletal Muscle and Is Capable of Activating Satellite Cells," *Developmental Biology*, 1998, 194:114-128.
Telusma, Gloria et al., "Dendritic Cell Activating Peptides Induce Distinct Cytokine Profiles," *International Immunology*, Nov. 2006, 18(11):1563-1573.
Thorey, Irmgard S. et al., "The $Ca^{2+}$-Binding Proteins S100A8 and S100A9 are Encoded by Novel Injury-regulated Genes," *The Journal of Biological Chemistry*, Sep. 21, 2001, 276(38):35818-35825.

(56) References Cited

OTHER PUBLICATIONS

Türker, Selcan et al., "Nasal Route and Drug Delivery Systems," *Pharmacy World and Science*, 2004, 26:137-142.
Uchida et al., "The Chemotactic Activity of PDGF-bb, BMP-2, and FGF-2 Towards Committed and Uncommitted Mesenchymal Stem Cells," *The Journal of Japanese Orthopaedic Surgical Society*, 2005, 79(8):S832, 1-P6-6.
Vandal, Karen et al., "Blockade of S100A8 and S100A9 Suppresses Neutrophil Migration in Response to Lipopolysaccharide," *The Journal of Immunology*, Sep. 1, 2003, 171(5):2602-2609.
Cole, John Sterling, "Pharmacologic Mobilization of Mesenchymal Stem Cells for Enhanced Bone Formation," Colby College, Rush University, 2009; UMI No. 1466383, pp. 1-82.
Kirov, Sergei A. et al., "In Vivo 2-Photon Microscopy Reveals G-CSF Enhanced Mobilization and Targeting of Neo-Endogenous Bone Marrow Stromal Cells to Stroke Injury Sites," *Stroke*, Apr. 2009, 40(4):1-2, e133, Abstract No. 107.
Straino, Stefania et al., "High-Mobility Group Box 1 Protein in Human and Murine Skin: Involvement in Wound Healing," *Journal of Investigative Dermatology*, 2008, 128:1545-1553.
Bianchi, M.E., "High mobility group 1 protein (HMGB1) N-terminal peptide." Geneseq Accession No. AD080180, Aug. 12, 2004.
Herrera, M.B., et al., "Exogenous mesenchymal stem cells localize to the kidney by means of CD44 following acute tubular injury," *Kidney International*, 2007; 72:430-441.
Tang, Daolin, et al., "High-Mobility Group Box 1, Oxidative Stress, and Disease," *Antioxidants & Redox Signaling*, 2011; 14(7): 1315-1335. DOI: 10.1089/ars.2010.3356.
Dong, Yingying et al., "HMGB1 Protein Does Not Mediate the Inflammatory Response in Spontaneous Spinal Cord Regeneration," *The Journal of Biological Chemistry*, Jun. 21, 2013, 288(25):18204-18218.
Kikuchi, Kiyoshi et al., "HMGB1 as a therapeutic target in spinal cord injury: A hypothesis for novel therapy development (Review)," *Experimental and Therapeutic Medicine*, 2011, 2:767-770.
Ulloa, Luis et al., "High-mobility group box 1 (HMGB1) protein: Friend and foe," *Cytokine & Growth Factor Reviews*, 2006, 17:189-201.
Venereau, Emilie et al., "Mutually exclusive redox forms of HMGB1 promote cell recruitment of proinflammatory cytokine release," *J. Exp. Med.*, 2012, 209(9):1519-1528.
Morosetti, R., et al., "MyoD expression restores defective myogenic differentiation of human mesoangioblasts from inclusion-body myositis muscle." *PNAS*, Nov. 7, 2006, 103(45):16995-17000.
Woodbury, Dale et al., "Adult Rat and Human Bone Marrow Stromal Cells Differentiate Into Neurons," *Journal of Neuroscience Research*, Aug. 15, 2000; 61(4):364-370.
Gong, Wei et al., "The Anti-Inflammatory Activity of HMGB1 A Box is Enhanced When Fused with C-Terminal Acidic Tail," *Journal of Biomedicine and Biotechnology*, vol. 2010, Article ID 915234, 6 pages, 2-10. Doi:10.1155/2010/915234.
Esposito, E., et al., "Melatonin reduces stress-activated/mitogen-activated protein kinases in spinal cord injury." *J. Pineal Res.*, 2009, 46: 79-86.
Healthwise Staff, "Age-related Macular Degeneration." University of Michigan Health System, Aug. 2015, https://www.uofmhealth.org/health-library/hw176039.
Jiao, C., et al., "Researchers find nerve damage may precede diabetic retinopathy." *EurekAlert! Science News*, Apr. 2016, https://www.eurekalert.org/pub_releases/2016-04/uoih-rfv042616.php.
Kawabata, H., et al., "High Mobility Group Box 1 Is Upregulated After Spinal Cord Injury and Is Associated With Neuronal Cell Apoptosis." *Spine*, 2010, 35(11): 1109-1115.
Slater, M., et al., "Endometriotic cells exhibit metaplastic change and oxidative DNA damage as well as decreased function, compared to normal endometrium." *Journal of Molecular Histology*, 2005, 36(4): 257-263.
Wolf, G., et al., "From the Periphery of the Glomerular Capillary Wall Toward the Center of Disease." *Diabetes*, Jun. 2005, 54(6): 1626-1634.
Arminan, Ana et al., "Mesenchymal Stem Cells Provide Better Results Than Hematopoietic Precursors for the Treatment of Myocardial Infarction." *JACC*, May 18, 2010, 55(20): 2244-2253.
Berry, Mark F., et al., "Mesenchymal stem cell injection after myocardial infarction improves myocardial compliance." *Am J Physiol Heart Circ Physiol*, Jun. 2006, 290(6): H2196-H2203.
HMGBiotech, "BoxA from HMGB1, human & mouse, LPS-free." *HMGBiotech Srl*, 2008, C.F. e P.IVA 04942740962, http://www.hmgbiotech.com/products.php?ID=91.
HMGBiotech, "BoxA from HMGB1, human & mouse LPS-free—Datasheet." *HMGBiotech Srl*, 2008, Via Moretto da Brescia 25, 20133—Milano, Italy, http://www.hmgbiotech.com/upload/documenti/0515122144_boxa.
Ishikane, Shin, "Therapeutic application of allogenic fetal membrane-derived mesenchymal stem cells transplantation in regenerative medicine." *Pharmaceutical Bulletin of Fukuoka University*, Mar. 2011, 11(0): 17-25.
Li, Ying et al., "Advancement of Human Multiply, Sex health and Reproductive Medical Science." *Peking University Medical Press*, Mar. 2007, 1st Edition, 270-271.
Takahashi, Kunihiko, et al., "Modulated Inflammation by Injection of High-Mobility Group Box 1 Recovers Post-Infarction Chronically Failing Heart." *Circulation*, Sep. 2008, 118(14 Suppl): S106-S114.
Wang, Wei et al., "Intravenous administration of bone marrow mesenchymal stromal cells is safe for the lung in a chronic myocardial infarction model." *Regen Med*, Mar. 2011, 6(2): 179-190.
Wang, Yaping, "Biology of hematopoietic stem cell and the research method thereof." *Science Press*, Mar. 2007, 1st Edition, 56-58.

\* cited by examiner

SEQUENCE LISTING

```
<160> NUMBER OF SEQ ID NOS: 3

<210> SEQ ID NO 1
<211> LENGTH: 215
<212> TYPE: PRT
<213> ORGANISM: Homo sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Glu
    210                 215
```

```
<210> SEQ ID NO 2
<211> LENGTH: 648
<212> TYPE: DNA
<213> ORGANISM: Homo sapiens

<400> SEQUENCE: 2
atgggcaaag gagatcctaa gaagccgaga ggcaaaatgt catcatatgc attttttgtg      60
caaacttgtc gggaggagca taagaagaag cacccagatg cttcagtcaa cttctcagag     120
ttttctaaga agtgctcaga gaggtggaag accatgtctg ctaaagagaa aggaaaattt     180
gaagatatgg caaaagcgga caaggcccgt tatgaaagag aaatgaaaac ctatatccct     240
cccaaagggg agacaaaaaa gaagttcaag gatcccaatg cacccaagag gcctccttcg     300
gccttcttcc tcttctgctc tgagtatcgc ccaaaaatca aggagaaca tcctggcctg     360 tccattggtg atgttgcgaa gaaactggga gagatgtgga ataacactgc tgcagatgac     420
aagcagcctt atgaaaagaa ggctgcgaag ctgaaggaaa aatacgaaaa ggatattgct     480
gcatatcgag ctaaaggaaa gcctgatgca gcaaaaaagg gagttgtcaa ggctgaaaaa     540
agcaagaaaa agaaggaaga ggaggaagat gaggaagatg aagaggatga ggaggaggag     600
gaagatgaag aagatgaaga tgaagaagaa gatgatgatg atgaataa                  648

<210> SEQ ID NO 3
<211> LENGTH: 44
<212> TYPE: PRT
<213> ORGANISM: Artificial sequence
<220> FEATURE:
<223> OTHER INFORMATION: Synthesized peptide from an HMGB1 protein

<400> SEQUENCE: 3

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys
        35                  40
```

METHOD FOR TREATING CARDIAC INFARCTION USING HMGB1 FRAGMENT

CROSS REFERENCE TO A RELATED APPLICATION

This application is a National Stage Application of International Application Number PCT/JP2013/078758, filed Oct. 24, 2013; which claims priority to Japanese Patent Application No. 2012-235785, filed Oct. 25, 2012; both of which are incorporated herein by reference in their entirety.

The Sequence Listing for this application is labeled "SeqList-17Apr15.txt", which was created on Apr. 17, 2015, and is 4 KB. The entire content is incorporated herein by reference in its entirety.

TECHNICAL FIELD

The present invention relates to novel pharmaceutical compositions for treating myocardial infarction comprising an HMGB1 fragment peptide, and uses thereof.

BACKGROUND ART

Acute myocardial infarction which results in the necrosis of cardiac muscle due to coronary artery occlusion is a disease with poor prognosis and is the main underlying condition for heart diseases which are the second cause of death in Japan. Existing therapies, acute phase catheterization and coronary artery bypass surgery, alleviate myocardial damage and contribute to the reduction of mortality rate; however, there are problems such as myocardial damage that occurs when the blocked coronary blood flow restarts (ischemia-reperfusion injury). Thus, development of further therapies is desired.

Recently, in basic experiments using animal models, bone marrow mesenchymal stem cell transplantation has been reported to suppress the development of myocardial infarction via regeneration of cardiac muscle by direct differentiation of the transplanted cells into constituent cardiac muscle cells, and also via suppression of left ventricular remodeling caused by the paracrine effect of the produced cytokines. Currently, clinical trials of autologous cell transplantations via various administration routes are being carried out. However, many issues remain to be resolved as problems concerning autologous cell transplantation, such as physical burden imposed at cell collection, cost and manpower involved in cell culturing, and the time required until cell transplantation. Meanwhile, it has been recently confirmed that a mechanism exists in which damaged tissue releases factors that recruit bone marrow pluripotent stem cells into blood to induce tissue regeneration at the damaged site. Tissue regeneration that uses the mechanism of inducing regeneration of damaged tissue in vivo by administering bone marrow stem cell-inducing factors is a non-conventional novel concept in regenerative therapy, and is believed to be advantageous compared to cell therapy that uses stem cells in that manpower is not required, stable supply is possible, and administration at an early stage of damage is possible.

In previous studies, the present inventors have identified the HMGB1 protein as a novel factor that mobilizes bone marrow pluripotent stem cells. HMGB1 is the major component of non-histone nuclear protein and is extracellularly released from dendritic cells, macrophages, or necrotic cells that accumulate in damaged sites, and is confirmed to be associated with various diseases.

PRIOR ART DOCUMENTS

Patent Documents

[Patent Document 1] WO2008/053892
[Patent Document 2] WO2007/015546
[Patent Document 3] WO2009/133939
[Patent Document 4] WO2009/133940
[Patent Document 5] WO2009/133940
[Patent Document 6] WO2004/004763
[Patent Document 7] WO2002/074337

Non-Patent Documents

[Non-patent Document 1] Bustin et al., Mol Cell Biol, 19: 5237-5246, 1999
[Non-patent Document 2] Hori et al., J. Biol. Chem., 270, 25752-25761, 1995
[Non-patent Document 3] Wang et al., Science, 285: 248-251, 1999
[Non-patent Document 4] Muller et al., EMBO J, 20: 4337-4340, 2001
[Non-patent Document 5] Wang et al., Science, 285: 248-251, 1999
[Non-patent Document 6] Germani et al., J Leukoc Biol., 81(1): 41-5, 2007
[Non-patent Document 7] Palumbo et al., J. Cell Biol., 164: 441-449, 2004
[Non-patent Document 8] Merenmies et al., J. Biol. Chem., 266: 16722-16729, 1991
[Non-patent Document 9] Wu Y et al., Stem cells, 25: 2648-2659, 2007
[Non-patent Document 10] Tamai et al., Proc Natl Acad Sci USA., 108(16): 6609-6614, 2011
[Non-patent Document 11] Yang et al., J Leukoc Biol., 81(1): 59-66, 2007

SUMMARY OF THE INVENTION

Problems to be Solved by the Invention

Recently, in diseases such as cerebral infarction, it has been confirmed that a mechanism exists in which damaged tissue induces tissue regeneration at the damaged site by releasing factors that mobilize bone marrow pluripotent stem cells into blood, and that the mechanism contributes to the prevention of further expansion of the damage. In the present invention, the present inventors aimed to develop novel therapeutic agents for myocardial infarction using fragment peptides derived from an HMGB1 protein, which was identified as a new bone marrow pluripotent stem cell mobilizing factor.

Means for Solving the Problems

The present inventors prepared a fragment peptide (1-44) of an HMGB1 protein which has a cell migration activity, and revealed in the myocardial infarction model for the first time that systemic administration of the fragment peptide enhances the accumulation of PDGFRα-positive cells in infarction sites and vicinities thereof. Further, long-standing improvement of the heart function was demonstrated in the myocardial infarction model animals administered with the fragment peptide (1-44). The above suggests that the fragment peptide (1-44) induces tissue regeneration by making use of the mechanism of inducing damaged tissue regeneration in vivo, and suppresses the development of acute myocardial infarction. Thus, it is shown that the fragment peptide of the present invention can be a useful therapeutic agent for poor-prognosis human acute myocardial infarction.

The present invention discloses novel pharmaceutical compositions for treating myocardial infarction comprising an HMGB1 fragment peptide, and uses thereof.

Specifically, the present inventors produced a peptide consisting of amino acids at positions 1 to 44 of an HMGB1 protein (SEQ ID NO: 3) by peptide synthesis. To model mice that enable evaluation of the therapeutic effect on myocardial infarction, each of the produced HMGB1 fragments was administered, and the therapeutic effects of the fragments on myocardial infarction were confirmed.

Based on these findings, the present application provides the following invention:

[1] a pharmaceutical composition for use in the treatment of myocardial infarction, comprising an HMGB1 fragment peptide;
[2] the pharmaceutical composition of [1], wherein the HMGB1 fragment peptide is a peptide comprising the amino acid sequence of SEQ ID NO: 3;
[3] the pharmaceutical composition of [1], wherein the HMGB1 fragment peptide is a peptide consisting of the amino acid sequence of SEQ ID NO: 3;
[4] a method for treating myocardial infarction, comprising the step of administering an HMGB1 fragment peptide;
[5] the method of [4], wherein the HMGB1 fragment peptide is a peptide comprising the amino acid sequence of SEQ ID NO: 3;
[6] the method of [4], wherein the HMGB1 fragment peptide is a peptide consisting of the amino acid sequence of SEQ ID NO: 3;
[7] an HMGB1 fragment peptide for use in the treatment of myocardial infarction;
[8] the HMGB1 fragment peptide of [7], wherein the HMGB1 fragment peptide is a peptide comprising the amino acid sequence of SEQ ID NO: 3;
[9] the HMGB1 fragment peptide of [7], wherein the HMGB1 fragment peptide is a peptide consisting of the amino acid sequence of SEQ ID NO: 3;
[10] use for the production of a medicament for use in the treatment of myocardial infarction, comprising an HMGB1 fragment peptide;
[11] the use of [10], wherein the HMGB1 fragment peptide is a peptide comprising the amino acid sequence of SEQ ID NO: 3; and
[12] the use of [10], wherein the HMGB1 fragment peptide is a peptide consisting of the amino acid sequence of SEQ ID NO: 3.

BRIEF DESCRIPTION OF THE DRAWINGS

FIG. 1B is a photograph showing immunofluorescence staining in the border site of a fragment peptide (1-44)-administered mouse. Cells positive for green fluorescence are GFP-positive bone marrow-derived cells and cells positive for red fluorescence indicate PDGFRα-expressing cells. Cells positive for both GFP and PDGFRα are indicated with arrows.

MODES FOR CARRYING OUT THE INVENTION

The present invention provides pharmaceutical compositions for use in the treatment of myocardial infarction, which comprises an HMGB1 fragment peptide having a cell migration-stimulating activity. Herein, pharmaceutical compositions for use in the treatment of myocardial infarction of the present invention are also expressed as medicaments, pharmaceutical agents, or medicinal compositions.

In the present invention, a cell migration-stimulating activity refers to the activity of stimulating cell migration. Herein, a cell migration-stimulating activity is also expressed as a cell migration-inducing activity or a cell-attracting activity.

The pharmaceutical compositions of the present invention can be administered/added to any sites. That is, the compositions can exert their effects no matter at which site they are administered, such as a site of myocardial infarction in need of regeneration, a site other than the infarction site, or blood. For example, when the compositions are administered/added, cells are recruited to the site of administration/addition or its nearby sites, thereby inducing or promoting regeneration of the lesion. Also, for example, when the compositions are administered/added to an infarction site or to the vicinity thereof, cells are recruited to the infarction site, thereby inducing or promoting regeneration of the infarction site. Further, for example, when the compositions are administered/added to a tissue other than a tissue in need of regeneration, bone marrow cells are mobilized from bone marrow to the site in need of regeneration through peripheral circulation, thereby inducing or promoting regeneration. Here, "peripheral circulation" is also called "blood circulation" or "peripheral circulation bloodstream".

Administration to a tissue other than a tissue in need of regeneration refers to administration to a site that is not a site in need of regeneration (a site other than a site in need of regeneration). Accordingly, "a tissue other than a tissue in need of regeneration" can also be referred to as: a site other than a tissue in need of regeneration; a site other than a site in need of regeneration; a site distant from a tissue in need of regeneration; a site distant from a site in need of regeneration; a site distal to a site in need of regeneration; a tissue distal to a tissue in need of regeneration; a distal site; or a distal tissue.

Thus, compositions of the present invention are effectively used to regenerate tissues to which it is difficult to directly administer pharmaceutical agents from outside of the body. Examples of the tissue other than a tissue in need of regeneration include blood tissues, muscle tissues, subcutaneous tissues, intradermal tissues, abdominal cavity, and such.

In the present invention, cells that are stimulated to migrate or cells mobilized from bone marrow to peripheral blood include undifferentiated cells and cells in various stages of differentiation, but are not limited thereto. In the present invention, cells that are stimulated to migrate or cells mobilized from bone marrow to peripheral blood include stem cells, non-stem cells, and such, but are not limited thereto. Stem cells include circulatory stem cells and non-circulatory stem cells. Non-circulatory stem cells are, for example, stem cells residing in a tissue. Circulatory stem cells are, for example, circulatory stem cells in blood.

Further, cells stimulated to migrate or cells mobilized from bone marrow to peripheral blood include bone marrow-derived cells and hematopoietic stem cells, but are not limited thereto. In the present specification, "hematopoietic stem cells" are stem cells that can differentiate into blood cells such as red blood cells, platelets, mast cells, and dendritic cells, as well as white blood cells including neutrophils, eosinophils, basophils, lymphocytes, monocytes, macrophages, and such. Their markers are known to be CD34-positive and CD133-positive in human, and CD34-negative, c-Kit-positive, Sca-1-positive, and lineage marker-negative in mouse. Hematopoietic stem cells are difficult to be cultured alone when cultured in culture dishes, and they need to be co-cultured with stromal cells.

In the present specification, "bone marrow cells" means cells present inside bone marrow while "bone marrow-derived cells" means "bone marrow cells" mobilized from bone marrow to outside of bone marrow. "Bone marrow cells" include cells containing tissue progenitor cell populations present inside bone marrow. Further, "bone marrow-derived cells" may be cells containing mesoangioblasts or cells free of mesoangioblasts.

Tissue progenitor cells are defined as undifferentiated cells having a unidirectional potency to differentiate into cells of a specific tissue other than the blood system, and include undifferentiated cells having the potency to differentiate into mesenchymal tissues, epithelial tissues, nerve tissues, parenchymatous organs, and vascular endothelium as mentioned above.

"Bone marrow cells" and "bone marrow-derived cells" are hematopoietic stem cells and differentiated cells derived therefrom such as leukocytes, erythrocytes, platelets, osteoblasts, and fibrocytes, or are stem cells represented by cells which have been hitherto called bone marrow mesenchymal stem cells, bone marrow stromal pluripotent stem cells, or bone marrow pluripotent stem cells. As used herein, "bone marrow stem cells" refer to stem cells present inside bone marrow, while "bone marrow-derived stem cells" refer to "bone marrow stem cells" mobilized from bone marrow to outside of bone marrow. In the present invention, cells stimulated to migrate or cells mobilized from bone marrow to peripheral blood include "bone marrow-derived stem cells", but are not limited thereto. "Bone marrow cells" and "bone marrow-derived cells" can be isolated by bone marrow collection (bone marrow cell collection) or peripheral blood collection. Hematopoietic stem cells are nonadherent, while some of the "bone marrow cells" and "bone marrow-derived cells" are obtained as adherent cells by means of a cell culture of a monocyte fraction of blood obtained by the bone marrow collection (bone marrow cell collection) or peripheral blood collection.

Moreover, "bone marrow cells" and "bone marrow-derived cells" include mesenchymal stem cells, and have a potential to differentiate into, preferably, osteoblasts (which can be identified by observing calcification after inducing differentiation), chondrocytes (which can be identified by alcian blue positive staining, safranin O positive staining, or the like), adipocytes (which can be identified by Sudan III positive staining), and other mesenchymal cells such as fibroblasts, smooth muscle cells, stromal cells, and tendon cells; and further nerve cells, epithelial cells (for example, epidermal keratinocytes and intestinal epithelial cells express cytokeratin family), and vascular endothelial cells. The cells to be differentiated into are not limited to the above cells, and the potential to differentiate into cells of parenchymatous organs such as liver, kidney, and pancreas is also included.

Herein, "bone marrow mesenchymal stem cells", "bone marrow stromal pluripotent cells" or "bone marrow pluripotent stem cells" refer to cells existing in the bone marrow, which are directly collected from the bone marrow or indirectly collected from other tissues (blood, skin, fat, and other tissues), and can be cultured and proliferated as adherent cells on a culture dish (made of plastic or glass). These cells are characterized in having a potential to differentiate into mesenchymal tissues such as bone, cartilage, and fat (mesenchymal stem cells), or into skeletal muscle, heart muscle, nervous tissues, and epithelial tissues (pluripotent stem cells), and can be obtained by collection of bone marrow cells.

On the other hand, "bone marrow-derived bone marrow mesenchymal stem cells", "bone marrow-derived bone marrow stromal pluripotent cells", or "bone marrow-derived bone marrow pluripotent stem cells" mobilized from bone marrow to outside of the bone marrow are cells that can be obtained by collection from peripheral blood, mesenchymal tissues such as fat, epithelial tissues such as skin, or nervous tissues such as brain.

In addition, these cells are also characterized in having a potential to differentiate into, for example, epithelial tissues such as keratinocytes that constitute skin, or nervous tissues that constitute brain, when administered to a lesion area of the living body immediately after collection or after once being adhered onto a culture dish.

Bone marrow mesenchymal stem cells, bone marrow stromal pluripotent stem cells, bone marrow pluripotent stem cells, or these cells recruited from bone marrow to outside of the bone marrow preferably have a potency to differentiate into: osteoblasts (which can be identified by observing calcification after inducing differentiation), chondrocytes (which can be identified by alcian blue positive staining, safranin O positive staining, or the like), adipocytes (which can be identified by Sudan III positive staining or the like), and other mesenchymal cells such as fibroblasts, smooth muscle cells, skeletal muscle cells, stromal cells, and tendon cells; nerve cells, pigment cells, epidermal cells, hair follicle cells (which express cytokeratin family, hair keratin family, or the like), epithelial cells (for example, epidermal keratinocytes and intestinal epithelial cells express cytokeratin family or the like), and endothelial cells; and further into cells of parenchymatous organs such as liver, kidney, and pancreas. However, differentiated cells are not limited to the above cells.

Human bone marrow cells and human bone marrow-derived cells can be exemplified by, but are not limited to, cells which can be directly obtained by collecting bone marrow (bone marrow cells), peripheral blood, or fat, or obtained as adherent cells through culturing of an isolated monocyte fraction. Markers for human bone marrow cells and human bone marrow-derived cells include, for example, all or some of the following but are not limited thereto: PDGFRα-positive, Lin-negative, CD45-negative, CD44-positive, CD90-positive, and CD29-positive, Flk-1-negative, CD105-positive, CD73-positive, CD90-positive, CD71-positive, Stro-1-positive, CD106-positive, CD166-positive, and CD31-negative.

Moreover, mouse bone marrow cells and mouse bone marrow-derived cells can be exemplified by, but are not limited to, cells which can be directly obtained by collecting bone marrow (bone marrow cells), peripheral blood, or fat, or obtained as adherent cells through culturing of an isolated monocyte fraction. Markers for mouse bone marrow cells and mouse bone marrow-derived cells include, for example, all or some of the following but are not limited thereto: CD44-positive, PDGFRα-positive, PDGFRβ-positive, CD45-negative, Lin-negative, Sca-1-positive, c-kit-negative, CD90-positive, CD29-positive, and Flk-1-negative.

In the present invention, cells stimulated to migrate include PDGFRα-positive cells, but are not limited thereto. In addition, PDGFRα-positive cells stimulated to migrate are not particularly limited, but preferably are bone marrow-derived PDGFRα-positive cells. Further, markers other than PDGFRα can be exemplified by all or some of CD29-positive, CD44-positive, CD90-positive, CD271-positive, CD11b-negative, and Flk-1-negative, but are not limited thereto. PDGFRα-positive cells include, but are not limited to, for example, PDGFRα-positive bone marrow-derived cells, PDGFRα-positive bone marrow-derived mesenchymal stem cells, tissue cells residing in PDGFRα-positive tissues (for example, fibroblasts and such), PDGFRα-positive bone marrow-derived cells obtained as adherent cells by means of cell culture of a monocyte fraction of blood obtained by bone marrow collection (bone marrow cell collection) or peripheral blood collection.

The HMGB1 protein in the present invention includes, but is not limited to, for example, a protein comprising the amino acid sequence of SEQ ID NO: 1 as a human-derived HMGB1 protein, and DNA encoding said protein includes, but is not limited to, for example, a DNA comprising the nucleotide sequence of SEQ ID NO: 2.

In the present invention, "an HMGB1 fragment peptide having a cell migration-stimulating activity" refers to a peptide consisting of a portion of an HMGB1 protein and having a cell migration-stimulating activity. Fragment peptides consisting of a portion of an HMGB1 protein of the present invention are not particularly limited as long as they have cell migration-stimulating activity, but are preferably HMGB1 fragment peptides comprising at least the amino acid sequence of positions 1 to 44 of the HMGB1 protein (SEQ ID NO: 3), which are fragment peptides having a cell migration-stimulating activity.

In the present invention, the HMGB1 fragment peptides having a cell migration-stimulating activity can be exemplified by the fragments below, without being limited thereto.

In the present invention, the HMGB1 fragment peptides having a cell migration-stimulating activity include HMGB1 fragment peptides that comprise the amino acid sequence of SEQ ID NO: 3 and have a cell migration-stimulating activity. Such fragment peptides include, without being limited thereto, for example, as an upper limit any arbitrary HMGB1-derived fragment peptide that comprise at least the HMGB1 fragment peptide (1-44) but do not contain the full-length HMGB1 protein.

In the present invention, HMGB1 fragment peptides having a cell migration-stimulating activity include the HMGB1 fragment peptide (1-44).

Methods for administering a composition of the present invention include oral administration and parenteral administration. Specifically, parenteral administration includes, but is not limited to, injection, transnasal administration, transpulmonary administration, transdermal administration, and such. As examples of injection, intravenous injection, intramuscular injection, intraperitoneal injection, subcutaneous injection, and such can be used to administer a composition of the present invention systemically or locally (for example, under the skin, in the skin, on the surface of skin, eyeball or palpebral conjunctiva, nasal cavity mucosa, intraoral mucosa and mucosa of the gastrointestinal tract, vaginal mucosa/intrauterine mucosa, damage site or such).

Methods of administering a composition of the present invention include, but are not limited to, for example, intravascular administration (intra-arterial administration, intravenous administration, or such), blood administration, intramuscular administration, subcutaneous administration, intradermal administration, intraperitoneal administration.

There is no limitation on the site of administration, and for example, it may be a tissue site in need of regeneration or its nearby region, a site different from the tissue in need of regeneration, or a site distant to and different from the tissue in need of regeneration. The site is, for example, in the blood (in arteries, in veins, or such), muscle, under the skin, in the skin, in the abdominal cavity, or such, without being limited thereto.

The method of administration may be appropriately selected according to the age and the symptoms of the patient. When a peptide of the present invention is administered, the dose per time of the peptide can be selected within a range of 0.0000001 mg to 1000 mg per kg body weight of a patient. Alternatively, the dose can be selected within a range of 0.00001 mg to 100000 mg per body of patient, for example. When administering cells secreting a peptide of the present invention or gene therapy vectors inserted with DNA encoding the peptide, they may be administered such that the amount of the peptide is within the above range. However, the dose of pharmaceutical compositions of the present invention is not limited thereto.

HMGB1 fragment peptides of the present invention can be obtained as recombinants by incorporating a DNA encoding the peptide into an appropriate expression system, or can be synthesized artificially. Pharmaceutical compositions of the present invention can be formulated according to the usual methods (for example, Remington's Pharmaceutical Science, latest edition, Mark Publishing Company, Easton, U.S.A), and may contain pharmaceutically acceptable carriers and additives together. Examples include surfactants, excipients, colorants, perfumes, preservatives, stabilizers, buffers, suspending agents, isotonizing agents, binders, disintegrants, lubricants, flow promoters, and flavoring agents, although they are not limited thereto and other common carriers may be appropriately used. Specific examples include light anhydrous silicic acid, lactose, crystalline cellulose, mannitol, starch, carmellose calcium, carmellose sodium, hydroxypropylcellulose, hydroxypropylmethylcellulose, polyvinylacetaldiethylamino acetate, polyvinylpyrrolidone, gelatin, medium-chain fatty acid triglyceride, polyoxyethylene hydrogenated castor oil 60, white sugar, carboxymethyl cellulose, corn starch, and inorganic salts.

All prior art documents cited herein are incorporated herein by reference.

Herein below, the present invention will be further illustrated with reference to Examples, but it is not to be construed as being limited thereto.

EXAMPLE 1

(Objective)

The therapeutic effect by systemic administration of the HMGB1 protein fragment peptide (1-44) is comprehensively evaluated using an acute stage myocardial infarction mouse model by means of cardiac physiology, histopathology, and molecular biology.

(Materials and Methods)

Bone marrow cells were collected from the thigh bone/lower leg bone of three-week-old mice (C57BL6-CAG-GFP transgenic mice), and the bone marrow cell suspension was administered (300 ml/mouse) to the tail vein of six-week-old mice (C57BL6) after irradiation (10GY) to produce bone marrow chimeric mice. Sixty days after bone marrow transplantation, left fourth interspace thoracotomy was performed under general anesthesia in the supine position, and the proximal left anterior descending coronary artery was ligated to produce an extensive myocardial infarction model (left anterior descending coronary artery/circumflex occlusion model). In making the HMGB1 protein low molecular, a fragment peptide (1-44) of the HMGB1 protein was developed in consideration of retaining the activity of recruiting bone marrow mesenchymal stem cells. At 6, 24, 48, 72, and 96 hours after infarction creation, the HMGB1 protein fragment peptide (1-44) (5 µg/300 µl), or 300 µl of PBS (negative control group) was administered five times to the tail vain. Mice were euthanized by administration of excess ketamine and xylazine, and their hearts were collected. After the tissues were embedded in OCT compound, cryosections of 5 µm thickness were prepared. Immunohistological studies were performed as follows by using an anti-mouse PDGFRα antibody. The PDGFRα Rabbit Anti-PDGF Receptor Alpha Antibody (Abeam, AB61219) was used as the primary antibody. The Alexa 555 Goat Anti-rabbit Antibody (Molecular Probes) was used as the secondary antibody, and 4,6-diamino-2-phenylinodole (DAPI, Molecular Probes) was used for nuclear staining. Confocal laser scanning microscope (FV300, Olympus) was used for photographing. Regarding the number of bone marrow-derived mesenchymal stem cells accumulated in the tissue, the number of cells positive for both GFP and PDGFRα present in all areas of randomly-selected 5 sections were determined and the mean value was calculated. Further, RNA was extracted from myocardial tissue using the RNeasy Kit (Qiagen) and cDNA was obtained by reverse transcription reaction using the Omniscript Reverse Transcriptase (Qiagen). Real-time PCR was performed with the Gene Amp(R) PCR System 9700 (Life Technologies Japan) using the above-mentioned cDNA as a template, and the levels of TNFα and IL-1β mRNA were determined as a ratio to the GAPDH mRNA level. Improvement in the cardiac function was evaluated by measuring the left ventricular end-diastolic diameter (LVDd: Dd), left ventricular end-systolic diameter (LVDs: Ds), and left ventricular ejection fraction (LVEF: EF) using the Vivid 7 Echocardiography System and 12-MHZ Transducer (General Electric).

Figure 1A:
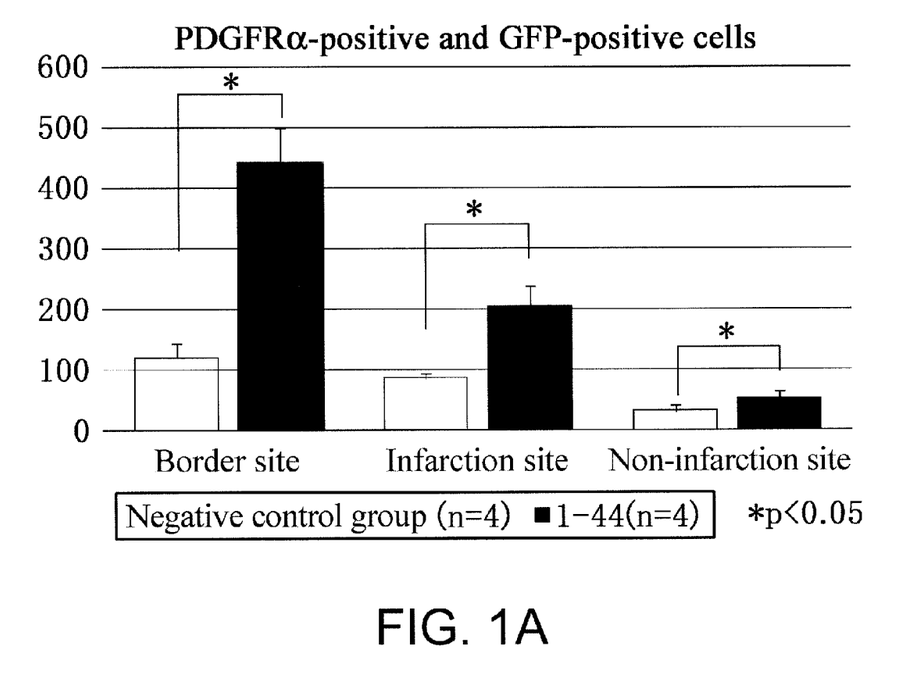
FIG. 1A is a graph indicating the number of PDGFRα-positive bone marrow mesenchymal stem cells in infarction sites (INFARCT), border sites (BORDER), and non-infarction sites (REMOTE) seven days after creating myocardial infarction. PDGFRα-positive bone marrow mesenchymal stem cells were significantly recruited (1-WAY ANOVA, *$P<0.05$ vs. 1-44) in all areas of the infarction, border, and non-infarction sites in the fragment peptide (1-44)-administered group (1-44; N=4) compared to the negative control group (CONT; N=4).

By systemic administration of the HMGB1 protein fragment peptide (1-44), PDGFRα-positive bone marrow-derived mesenchymal cells were recruited significantly in all areas of non-infarction sites, boundary sites, and infarction sites on day 7 post infarction creation (non-infarction site: partial fragment of the HMGB1 protein (1-44 peptide), $52\pm11\#*$; negative control, $32\pm9$ cells/mm$^2$, N=4 each, #P<0.05 vs. negative control) (FIG. 1A). Further, in the HMGB1 protein fragment peptide (1-44) group, the levels of inflammatory cytokines (TNFα, IL-1β) in the non-infarction sites were significantly low (TNFα: HMGB1 protein fragment peptide (1-44), $4\pm2\#*$; negative control, $11\pm3$ GAPDH; N=4 each, #P<0.05 vs. negative control), (IL-1β: HMGB1 protein partial fragment (1-44 peptide), $2\pm1\#*$; negative control, $6\pm1$ GAPDH; N=4 each, #P<0.05 vs. negative control) (FIGS. 1C, 1D). Ultrasonic examination of the heart on Day 56 revealed that left ventricular systolic dysfunction after myocardial infarction was significantly suppressed in the HMGB1 protein fragment peptide (1-44) group (EF: HMGB1 protein fragment peptide (1-44) (N=8), $26\pm4\#*$; negative control (N=16), $20\pm4\%$, #P<0.05 vs. negative control). Further, left ventricular enlargement was significantly suppressed in the HMGB1 protein fragment peptide (1-44) group (DD: HMGB1 protein fragment peptide (1-44) (N=8), $5.8\pm0.2\#*$, negative control (N=16), $6.3\pm0.2$ mm, #P<0.05 VS. negative control) (FIG. 1E).

Figure 1B:
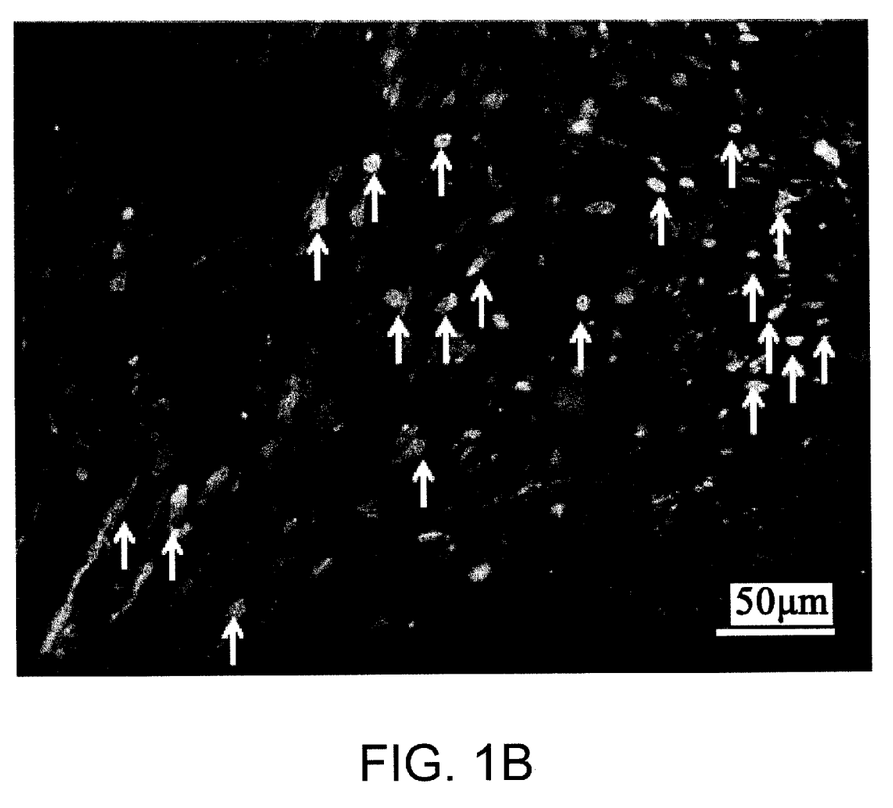
Figure 1C:
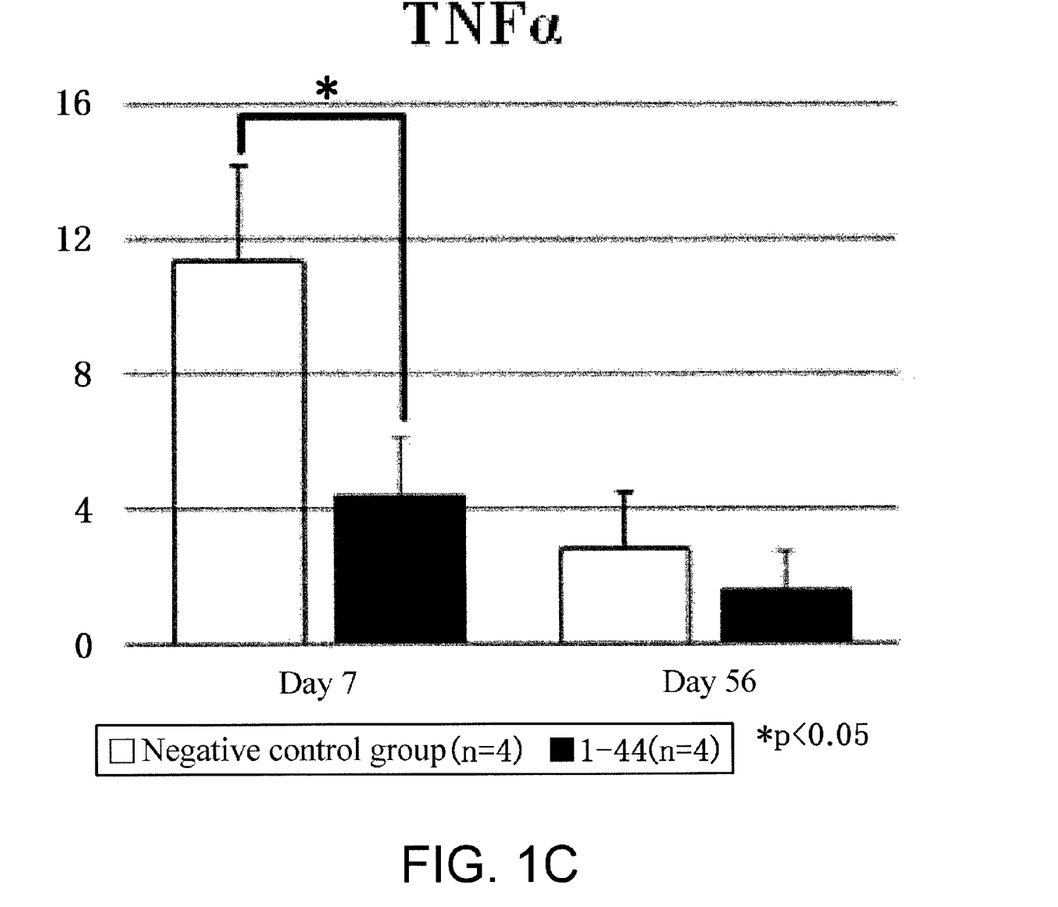
FIG. 1C is a graph showing the mRNA level of inflammatory cytokine TNFα in infarction sites (INFARCT), border sites (BORDER), and non-infarction sites (REMOTE) 7 and 56 days after creating myocardial infarction. The inflammatory cytokine (TNFα, IL-1β) levels in non-infarction sites were significantly lower (1-WAY ANOVA, #$P<0.05$ 1-44 vs. CONT) in the fragment peptide (1-44)-administered group (1-44; N=4) compared to the negative control group (CONT: N=4).
Figure 1D:
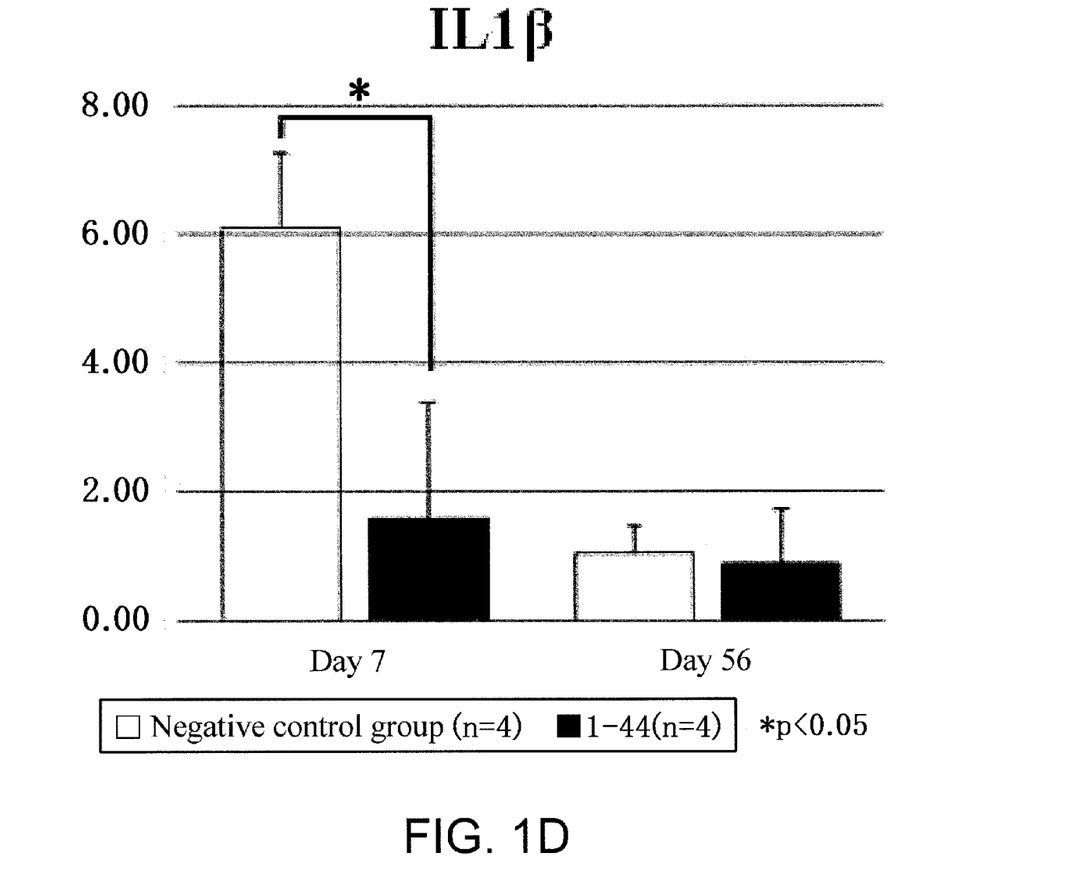
FIG. 1D is a graph showing the mRNA level of inflammatory cytokine IL-1β in infarction sites (INFARCT), border sites (BORDER), and non-infarction sites (REMOTE) 7 and 56 days after creating myocardial infarction. The inflammatory cytokine (TNFα, IL-1β) levels in non-infarction sites were significantly lower (1-WAY ANOVA, #$P<0.05$ 1-44 vs. CONT) in the fragment peptide (1-44)-administered group (1-44; N=4) compared to the negative control group (CONT: N=4).
Figure 1E:
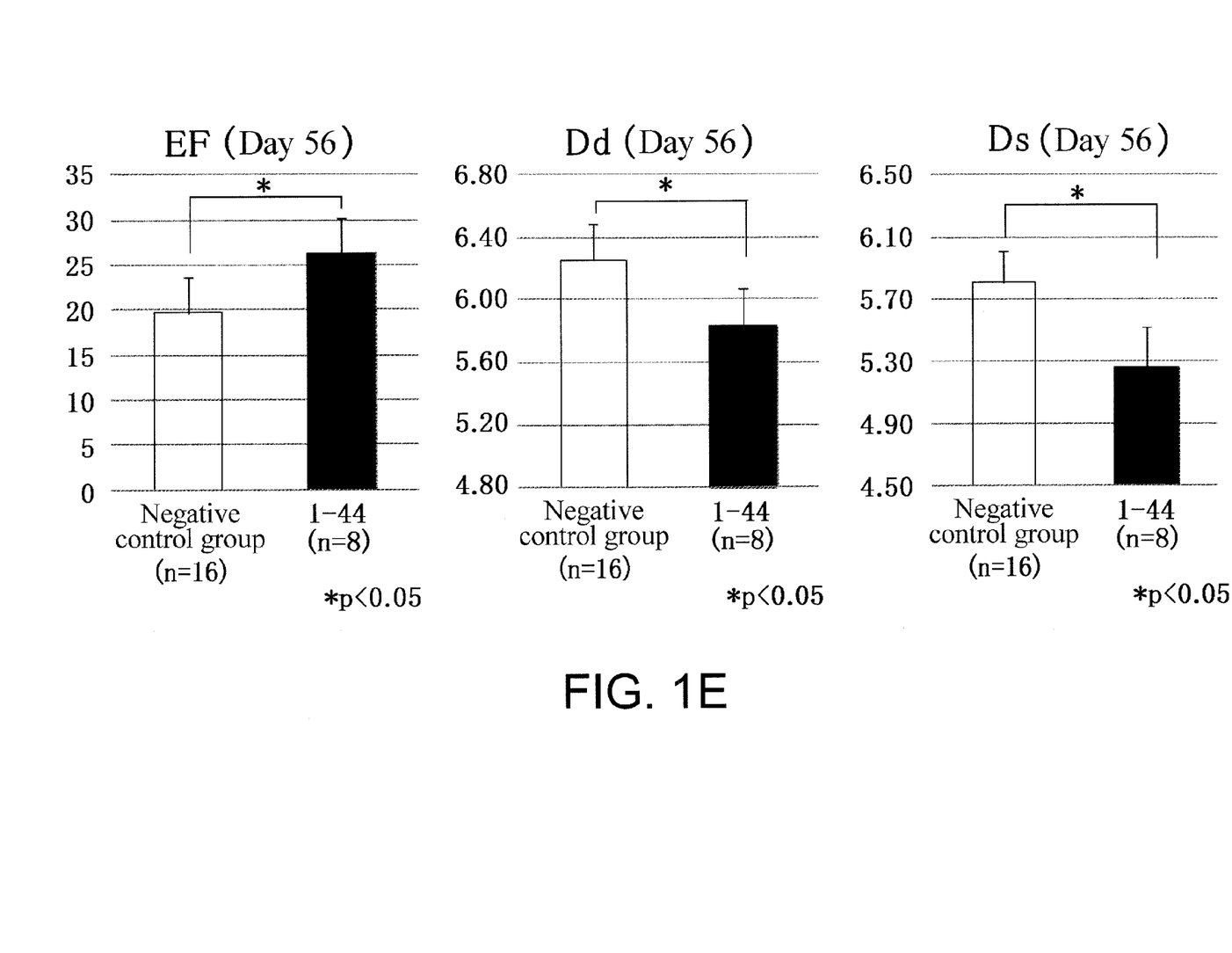
FIG. 1E is a graph showing the left ventricular ejection fraction (EF), left ventricular end-diastolic diameter (DD), and left ventricular end-systolic diameter (DS) of the negative control group and the fragment peptide (1-44)-administered group 56 days after creating myocardial infarction.

In the present investigation, it was demonstrated that five-day-administration of the HMGB1 protein fragment peptide (1-44) recruits PDGFRα-positive bone marrow mesenchymal stem cells to the infarction site and its neighboring region in the acute stage (Day 7) after infarction creation (FIGS. 1A, 1B). In particular, it was demonstrated that administration of the fragment peptide (1-44) enhances the recruitment of PDGFRα-positive mesenchymal stem cells to the myocardial tissue of the non-infarction site. Bone marrow mesenchymal stem cells are known to have an inflammation-suppressing effect and a tissue-regenerating effect. In the present Example, they were also found to suppress inflammatory reactions (FIGS. 1C, 1D). Further, administration of the HMGB1 fragment peptide (1-44) significantly suppressed the aggravation of the left ventricular systolic function, left ventricular enlargement, and left ventricular remodeling. Significant long-standing improvement of the myocardial function was also observed (FIG. 1E).

INDUSTRIAL APPLICABILITY

The present invention provides novel uses of HMGB1 fragment peptides that retain the activity of recruiting PDGFRα-positive cells for treating myocardial infarction. The HMGB1 fragment peptides of the present invention include fragment peptides with a molecular weight of about 20 percent of the full-length HMGB1 protein consisting of 215 amino acids. Such fragment peptides can be produced by chemical synthesis using peptide synthesizers, and are thus expected to improve purity, provide stable production, and reduce costs in the situation of producing peptides as pharmaceuticals.

Moreover, full-length HMGB1 is known to have an activity to bind to lipopolysaccharides (LPS) which are one type of endotoxin. Contamination of even a trace amount of LPS in pharmaceuticals causes fever and such, and often results in serious side effects. Thus, LPS contamination in pharmaceuticals is strictly regulated. As HMGB1 has affinity for LPS, it is difficult to completely eliminate LPS from pharmaceuticals contaminated therewith. However, making HMGB1 into peptides reduces its affinity to LPS, and thus it is expected to reduce LPS contamination in pharmaceuticals. Accordingly, by using an HMGB1 fragment comprising the portion for recruiting PDGFRα-positive cells as specified in the present invention, it is possible to develop safer pharmaceutical compositions for treating myocardial infarction.

Direct administration of the HMGB1 fragment peptide of the present invention to the myocardial infarction site in need of regeneration, or to the vicinity thereof, may induce or enhance regeneration of the infarction site or the tissue damaged by the infarction. Further, regeneration of myocardial infarction may be induced or enhanced by administering the HMGB1 fragment peptide of the present invention to a site different from the site in need of regeneration by means such as intravenous administration. As such, the present invention enables treatment of myocardial infarction with intravenous administration, which is widely performed in general practice; and thus, therapeutic agents can be safely and easily administered at arbitrary concentrations for an arbitrary number of times. This fact is one of the extremely superior aspects of the present invention in comparison to conventional therapeutic methods.

In current practice of regenerative medicine or cell therapy, scarce bone marrow pluripotent stem cells derived from patients are cultured ex vivo and used for therapies after proliferation; however, since the culturing process carries the risk of cell deterioration (canceration or contamination of bacteria, viruses, and such), sufficient safety control is required. In contrast, therapeutic agents based on the present invention do not include the step of taking cells outside the body or the step of including manual operation, and thus, they are believed to be relatively safe. This fact is also one of the superior aspects of the present invention in comparison to conventional therapeutic methods.

The invention claimed is:

1. A method for treating myocardial infarction in a subject, wherein said method comprises administering, to a subject in need of such treatment, an HMGB1 fragment peptide consisting of the amino acid sequence of SEQ ID NO: 3.

* * * * *